United States Patent [19]

Richard

[11] Patent Number: 4,834,110

[45] Date of Patent: May 30, 1989

[54] SUCTION CLAMPED TREATMENT CUP SALIVA SAMPLER

[76] Inventor: Patricia A. Richard, 100 Sandpiper Cir., Milford, Conn. 06460

[21] Appl. No.: 151,101

[22] Filed: Feb. 1, 1988

[51] Int. Cl.$^4$ ............................................... A61B 5/00
[52] U.S. Cl. .................................... 128/760; 604/176; 604/327
[58] Field of Search ................ 128/760, 768, 399–402; 604/176, 289, 290, 312, 313, 325, 327, 328, 369

[56] References Cited

U.S. PATENT DOCUMENTS

| | | |
|---|---|---|
| 2,146,472 | 6/1939 | Heintz et al. |
| 2,238,541 | 7/1941 | Spagnolo . |
| 2,655,145 | 11/1953 | Heger . |
| 2,972,346 | 2/1961 | Eddings ............................... 604/313 |
| 3,048,175 | 7/1962 | Uddenberg . |
| 3,315,665 | 4/1967 | MacLeod . |
| 3,379,192 | 2/1968 | Warren . |
| 3,382,867 | 12/1968 | Reaves . |
| 3,587,567 | 11/1971 | Schiff . |
| 3,608,540 | 10/1971 | Sartorius . |
| 4,048,990 | 8/1977 | Goetz . |
| 4,111,192 | 7/1978 | Wu . |
| 4,334,538 | 6/1982 | Juhn ..................................... 128/760 |
| 4,413,994 | 11/1983 | Sakshina ............................. 604/327 |
| 4,455,140 | 6/1984 | Joslin ................................... 128/760 |
| 4,768,238 | 9/1988 | Kleinberg et al. .................. 128/760 |

OTHER PUBLICATIONS

Wagner & Slavik, *An Individualized Plastic Intraoral Device for the Collection of Human Parotid Saliva*, Int'l J. of Clinical Pharmacology; Therapy & Toxicology, vol. 22, pp. 236, 239, (1984).

Meyer & Turner, *Devices for Collecting Separated Saliva*, N.Y. State Dent. J., 17:516–518, (1951).

Primary Examiner—Max Hindenburg
Attorney, Agent, or Firm—Mattern, Ware, Stoltz & Fressola

[57] ABSTRACT

A selective collector of a human patient's saliva for monitoring or analysis is formed as a substantially conical flat concave cup of resilient molded polymer with tubing connections at an apex portal, and a large entrance portal having a soft compliant foam elastomer rim positioned for contact with the patient's soft tissue, such as the interior of the patient's cheek around the parotid salivary duct.

Suction is connected to the soft foam rim, holding the concave cup in position, and suction, fixed pressure, pulsing pressure or electrical stimulation may promote the flow of saliva to a collector vessel. Medication may be administered to the patient's soft tissue if desired throug the entrance portal.

12 Claims, 2 Drawing Sheets

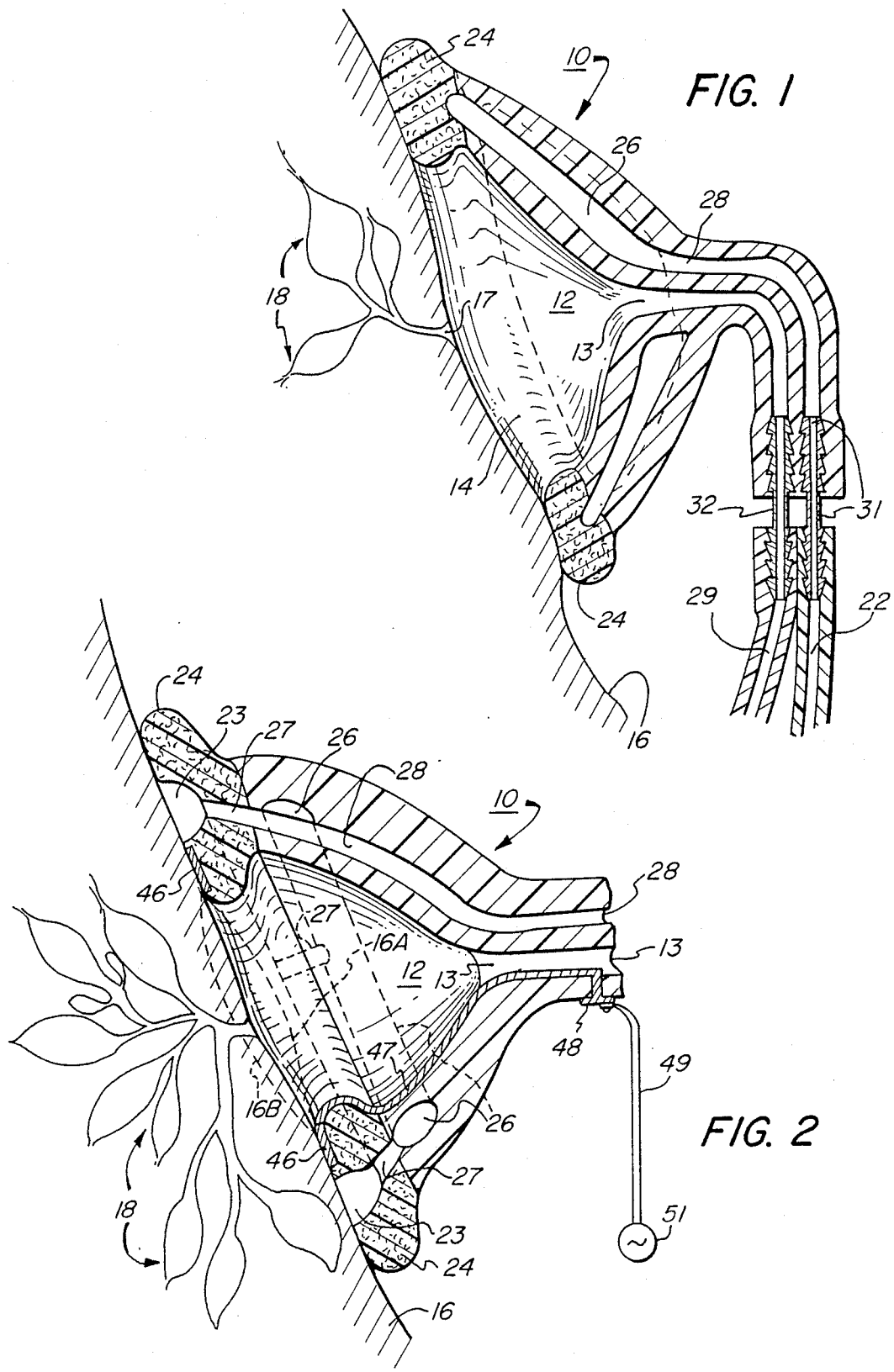

SUCTION CLAMPED TREATMENT CUP SALIVA SAMPLER

This invention relates to methods and devices for treatment of the human body, and particularly to intraoral sampling devices for collecting selected saliva samples from human patients conveniently and efficiently.

While suction drain tubings have been used for many years to withdraw secreted saliva from the mouths of dental patients to facilitate dental treatment, it has been found that the collection and analysis of selected samples of the patient's saliva provide detailed and sensitive information about the patient's condition and metabolism. In particular, blood levels of many different drugs may be quickly determined by this saliva analysis, and the condition of patients before and after kidney dialysis can be monitored readily by this technique. In space medicine, the real time condition of astronauts and their current drug blood levels can be monitored conveniently and indeed automatically by such techniques.

Many different proposals have described various kinds of saliva samplers, but these have been unsatisfactory for various reasons such as the cost of custom molded concave sampler cups, or the size, shape or rigidity of standardized sampler cups with hard metal rims, for example.

The samplers of the present invention are resilient and flexible, minimizing discomfort to the patient. In addition, they are provided with soft foam rims positioned for facing contact with the patient's soft tissue inside the mouth. Being small and flexible, they are easily maneuvered to the precise position desired for collection of parotid saliva issuing from Stensen's duct inside the patient's cheek, for example. In addition, their small size and flexible shape makes them suitable for use with different patients, and no custom fitted molding is required to fabricate the sampler for an individual patient.

The samplers of this invention are peripherally held in place by a gentle suction applied through porous foam encircling the rim of the sampler cup, or through a groove channel formed in the foam rim. Being firmly positioned in place by this means, the central cavity of the sampler may then be used for many different purposes. Medication may be introduced through the central cavity, saliva may be withdrawn therethrough, and the production of saliva may be encouraged by gentle pulsing fluctuation in the internal pressure in this central cavity, gently drawing up and depressing the soft tissue surrounding the parotid duct opening and thereby encouraging the flow of saliva to be collected and tested. If desired, a mild electrical current may be applied to the tissue through a peripheral electrode formed of metallic foil positioned in the surface of the foam rim of the sampler facing and in contact with the patient's soft tissue. This foil electrode is connected through suitable conductive leads to a conductor extending with the plural tubing from the sampler to the collector zone outside the patient's mouth. In this collector zone there are located an electrical current source, a saliva collector vessel, suitable partial vacuum sources and fluctuating pressure producing pumps, respectively connected to the tubing communicating with the soft foam rim of the sampler and with the sampler's central cavity, which latter may also receive medication through suitable valve connections with this tubing.

Warren U.S. Pat. No. 3,379,192 discloses a fluid delivery and withdrawal device with a custom mouthpiece embracing the patient's upper teeth or lower teeth, supplying water or solutions of dentifrice or medications directly to the tooth surfaces, and sluicing it away through suction outlets. The mouthpiece is of soft, resilient material, custom molded to fit each individual patient.

A comparable custom-molded thermoplastic dental implement for collecting patients' saliva is described by Wagner and Slavik, *An Individualized Plastic Intraoral Device for the Collection of Human Parotid Saliva*, Int'l J. of Clinical Pharmacology; Therapy and Toxicology, Vol. 22 pp. 236-239 (1984). This device is a hollow "collecting vessel" placed with its opening facing the parotid orifice and compressed to create a slight suction. Five-minute collection periods produce useful samples of parotid saliva.

Several other technical articles describe saliva collection devices, such as Meyer and Turner, *Devices for Collecting Separated Saliva*, N.Y. State Dent. J. 17: 516-518 (1951); Kutscher, Zegarelli et al, *A New Saliva Collection Technique for More Accurate Determination of Salivary Flow Rate*, N.Y. State Dent. J. 30: 63-64 (1964); Shannon et al, *Modified Carlson-Crittenden Device for Collection of Parotid Fluid*, J. Dent. Res. 41: 126-128 (1965); Schaefer et al, *A Plastic Intraoral Device for the Collection of Human Parotid Saliva*, J. Dent. Res. 56(7): 728-733 (1977).

The Meyer, Kutscher and Shannon articles all describe parotid saliva collection samplers fitting over Stensen's duct inside the patient's cheek, held in place by spring pressure or a rigid suction ring surrounding the sampler, and draining the sample through tubing for collection. The 1977 Schaefer article describes a concave unitary sampler with no tubing, said to be simpler to use and equally reliable. The Meyer, Kutscher and Schaefer devices are standardized shapes used for all patients, while the Shannon sampler employs a custom-shaped personal "parotid cap" of polymerized acrylic.

The dental implements proposed by Wagner and Slavik and by the Warren patent are also custom molded to fit individual patients, and no suction clamping or electrodes are suggested.

None of these prior art items suggests the administration of medication via those saliva samplers, or a soft resilient foam suction rim, or pulsing positive and negative fluctuating pressure, or the use of electrodes to stimulate the secretion of parotid saliva.

Schiff U.S. Pat. No. 3,587,567 discloses a heart massage device for use during open heart surgery incorporating an electrode for monitoring electrocardiac signals and additional alternative electrodes for performing fibrillation and defibrillation functions, but this heart massage machine is far different from the saliva samplers of this invention. A different kind of electrode is mounted on the central column of the treatment device shown in Heger U.S. Pat. No. 2,655,145 "to stimulate circulation of blood" in the scalp or other parts of the body, but Heger's electrode is a single rigid column device extending axially down the center of a treatment bell of substantial size, totally unsuitable for saliva sampling.

The introduction of medication to a patient's treatment site is suggested in McCloud U.S. Pat. No. 3,315,665, showing a skin massage device, and in an atomizer in the top of the Heger's bell for scalp and skin, and through the close-fitting, tooth-embracing custom molded device of the Warren patent, where fluid is delivered to and withdrawn from the surfaces of the teeth.

None of these prior art items mentioning the introduction of medication or the use of electrodes have suggested or even hinted that the medication or electrodes may usefully be combined with the saliva sampling operation or employed with saliva samplers such as those in the present invention.

Accordingly, the principal object of the invention is to provide a selective sampler for collecting saliva secreted by a patient for analysis.

Another object is to provide such samplers which are small in size, resiliently flexible and standardized in shape requiring no custom fitting for use by an individual patient.

A further object of the invention is to provide such saliva samplers equipped with soft flexible foam elastomer rims through which a partial vacuum may be drawn to provide suction positioning of the sampler at the precise location desired, such as Stensen's duct for the collection of parotid saliva, or the submaxillary or sublingual ducts.

Still another object of the invention is to provide such saliva samplers adapted to provide gentle pulsing pressure fluctuations in the central chamber alternately drawing up and depressing the patient's soft tissue surrounding the salivary duct opening for gently promoting the flow of saliva.

A further object of the invention is to provide such samplers incorporating a peripheral flexible metallic foil electrode for delivering mild electrical currents to the patient's soft tissue while the device is held in position.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

For a fuller understanding of the nature and objects of the invention, reference should be made to the following detailed description taken in connection with the accompanying drawings, in which:

THE DRAWINGS

FIG. 1 is a fragmentary cross-sectional elevation view, much enlarged, of a first embodiment of the saliva sampler intraoral cap of the present invention.

FIG. 2 is a similar cross-sectional side elevation view, much enlarged, of a different embodiment of the saliva collection cap of the present invention.

THE BEST MODE OF CARRYING OUT THE INVENTION

Figure 3:
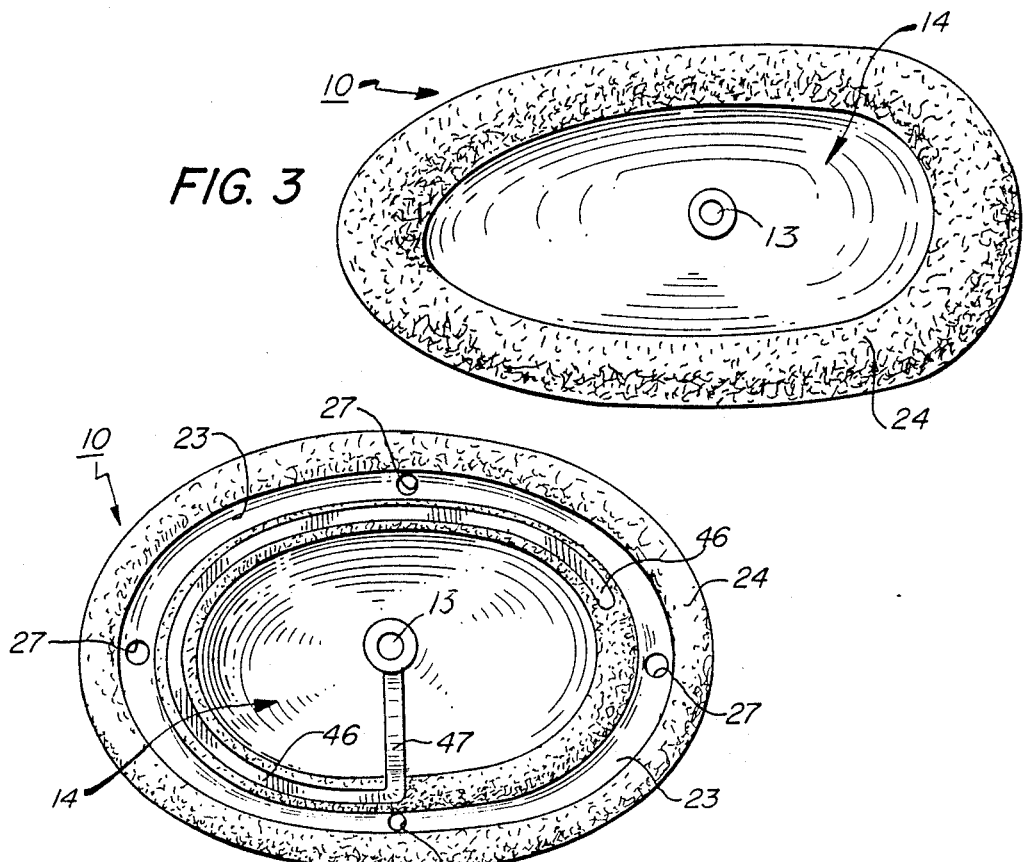
FIG. 3 is a front elevation view of the sampling face of the cap shown in FIG. 1.

The saliva samplers illustrated in the drawings incorporate the features believed to be most significant in achieving successful sampling of the patient's saliva with the present invention. All of the saliva samplers in the present invention incorporate a concave sampler cup 10 having an interior cavity 12 with an inner portal 13 at its inner apex. The outer exposed portal 14 of each cup 10 is formed as a circular or elliptical entrance portal 14 preferably having a soft foam rim 24. Both the soft foam rim and the concave sampler cup 10 itself are preferably formed of elastomers which may be molded in standard shapes, substantially like those illustrated in FIGS. 1 and 2, without requiring custom molding to fit individual patients. As shown in FIGS. 1 and 2, the soft foam rim 24 may be pressed firmly and compliantly against the soft tissue 16 inside the patient's cheek, with portal 14 enclosing the outlet 17 of the parotid salivary duct. Exemplary internal structure of the salivary glandular tissue delivering saliva to the outlet 17 is generally indicated at 18 in figures.

The soft foam suction rim 24 encircling entrance portal 14 is preferably connected to a suction blower 19 through a suitable valve 21 by way of a suction tube 22. Tube 22 is connected by way of an apex port 28 to a suction plenum 26 formed inside the body of the concave cup 10. Suction plenum 26 may take the form of a conical cavity, as illustrated in FIG. 1, or a ring-shaped cavity as shown in FIG. 2. As indicated in FIG. 1, the conical suction plenum cavity 26 extends outward within the walls of concave cup 10 to connect directly with the soft foam rim 24 encircling the entrance portal 14 of the cup 10. The soft foam rim 24 is preferably formed of open-cell foam, providing interstices and passageways therethrough, so that atmospheric pressure outside cap 10 within the patient's mouth coacts with the suction to maintain cap 10 in its desired location.

In the alternative embodiment shown in FIG. 2, soft foam rim 24 is formed with a central groove 23 extending around its entire length. Groove 23 is connected through suction passages 27 to suction plenum 26. In the embodiments incorporating groove 23, the soft foam rim 24 may be formed of closed cell foam if desired, thus enhancing the suction holding characteristics of groove 23 to stabilize the position of the concave cup 10 in its desired location.

The various functions performed by the concave cups of the present invention are achieved through different connections to the internal sampling chamber 12 by way of inner apex portal 13 and the sampling tube 29 to which it is connected. As indicated in FIG. 1, tubes 22 and 29 may be connected by tubing adapters 31 and 32 to respective apex suction port 28 and inner apex portal 13, quickly facilitating the connection of fresh concave sampler cups 10 successively through tubings 22 and 29 to the remainder of the system.

The small size and simplicity of construction of concave cups 10 permits them to be readily and inexpensively molded of moldable polymers in standard sizes, suitable for use by patients having different size mouths, and if sterilization of a concave cup is impractical, they may be readily discarded and a new sterile cup may be installed for use by the next patient.

Sampling tube 29 is connected directly through a flow measuring sensor 33 to a collector 34 in collector zone 35, from which the collected specimen 36 may be drained for analysis through valve 37 whenever desired. By connecting the upper portion of collector 34 above the level of saliva specimen 36 to the intake of suction blower 19, the flow of collected saliva in chamber 12 through portal 13 and sampling tube 29 is promoted by the resulting pressure differential between the atmospheric pressure in collecting chamber 12 and the reduced pressure in collector 34.

A selector valve 38 interposed in sampling tube 29 connects chamber 12 alternatively either to a medication supply source 39, or direct to the collector 34. Beyond selector valve 38 is a pressure conduit 41 connected to tubing 29 and delivering pressure through a selector valve 42 either at a constant pressure supplied by a constant pressure source 43 or at a pulsing pressure supplied by a pulsing pressure source 44.

When chamber 12 is connected to pulsing pressure source 44, the portion of the patient's soft tissue 16 exposed to the interior of chamber 12 is drawn in and depressed between two limit positions, such as positions 16A and 16B shown in FIG. 2, thus gently manipulating and massaging the parotid duct portal 17 to stimulate the flow of saliva therefrom into chamber 12.

Figure 4:
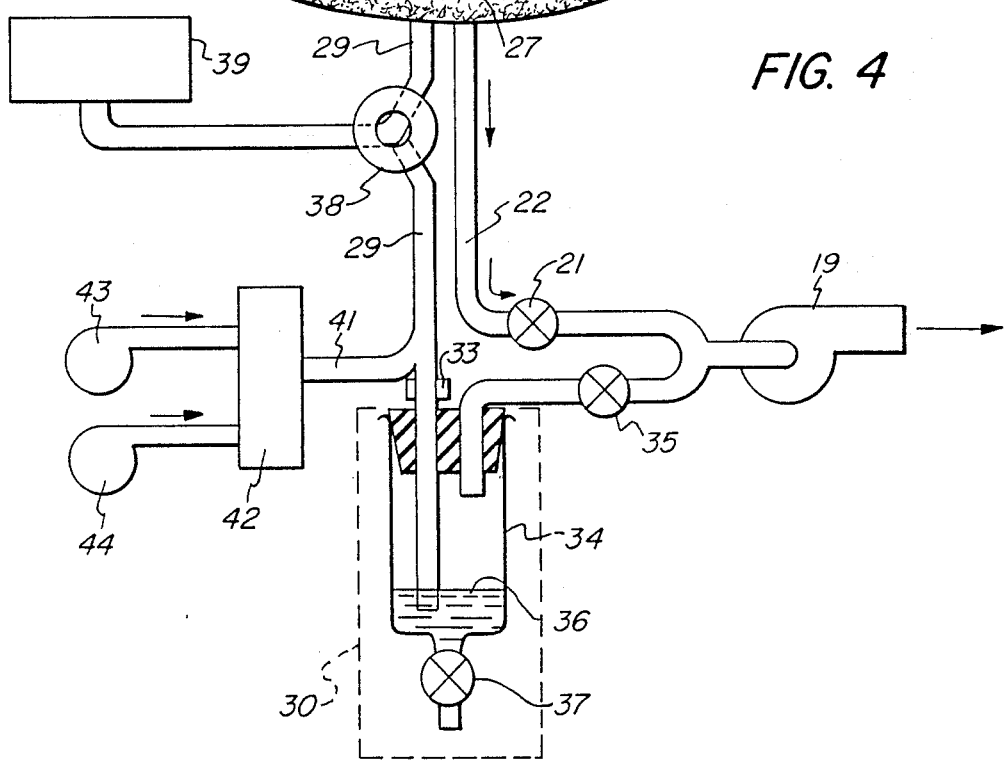
FIG. 4 is a corresponding front elevation view of the sampler cap shown in FIG. 2 connected to the remaining components of the system comprising the samplers of the present invention, and illustrating the tubing and sources of pressure and partial vacuum incorporated in these systems.

Finally, as shown in FIGS. 2 and 4, a thin flexible metal foil electrode 46 may be mounted extending all or part way around the periphery of the soft foam rim 24 inside its central groove 23 directly facing the patient's soft tissue 16, for contact therewith. Electrode 46 is connected by a similar strip of flexible conductive foil 47 cemented to the interior surface of cavity 12 inside concave cup 10 extending through apex portal 13 to a position inside the narrow apex of the cup where it may be connected by a suitable rivet connector 48 to the exterior of cup 10. Connector 48 is connected by suitable means such as a conductor 49 to a current source 51 providing a mild electric current to stimulate the tissues 16 in contact with foil electrode 46.

By these various means, the patient's soft tissue 16 may be exposed to medication from medication source 39, to pulsing pressure from pulsing pressure source 44, to a constant pressure from constant pressure source 43, and to a mild electrical stimulation through electrode 46. These are all applied through chamber 12 while concave cup 10 is held in the desired position, in contact with the soft tissue 16, by suction drawn through soft foam rim 24, plenum 26, apex suction port 28, suction tube 22 and valve 21 by suction blower 19 to the atmosphere. All of these various functions of positioning, stimulation, saliva collection and medication delivery are thus all performed by the single compact concave cups of the present invention.

It will thus be seen that the objects set forth above, and those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A flexible, resilient saliva sampler comprising in combination
    A. A suction blower,
    B. A hollow concave cap having an interior chamber bounded by a large entrance portal and a small inner portal,
    C. Means forming a soft flexible rim of elastomer foam material encircling the entrance portal and facing outward for depressible abutting engagement with the soft tissue of a human patient,
    D. First sampling conduit means connecting the inner portal to an external collector zone, and
    E. Second suction conduit means connecting the soft flexible rim encircling the entrance portal to the suction blower, whereby suction created by the blower holds the soft flexible elastomer foam rim against the patient's soft tissue, encircling a salivary duct outlet, and secreted saliva is collected in the interior chamber for delivery down the sampling conduit.

2. The combination defined in claim 1, wherein the soft foam rim is formed of open-cell foam.

3. The combination defined in claim 1, wherein the soft foam rim is formed with a central outward facing peripheral groove dividing it into an inner rim and an outer rim both facing the patient's soft tissue, with the second suction conduit means opening directly into the peripheral groove.

4. The combination defined in claim 1 further including means forming a suction plenum in the concave cup connected to the suction blower, and a plurality of suction passages joining the plenum to the soft flexible rim.

5. The combination defined in claim 1 further including a collector vessel in the collector zone, directly connected to the distal end of the sampling conduit means.

6. The combination defined in claim 5, further including a flow measuring unit operatively connected to the sampling conduit between the concave cap and the collector vessel.

7. The combination defined in claim 5, further including a valve connecting the suction blower to the collector vessel whereby a pressure differential is created promoting the delivery of collected saliva through the sampling conduit to the collector vessel.

8. The combination defined in claim 5, further including means forming a pressure conduit connected to the sampling conduit, and a pressure source connected to the pressure conduit.

9. The combination defined in claim 8, wherein the pressure source is a pulsing pressure source, supplying fluctuating pressure via the pressure conduit and the sampling conduit to the interior chamber, whereby the patient's soft tissue surrounding the salivary duct outlet is massaged.

10. The combination defined in claim 9, further including a separate fixed pressure source, and selector valve means alternatively connecting the pressure conduit either to the pulsing pressure source or the fixed pressure source.

11. The combination defined in claim 1, further including a medication source, and a selector valve interposed in the sampling conduit alternatively connecting the interior chamber either to the medication source or to the collector zone.

12. The combination defined in claim 1, further including an external current source, a thin flexible metallic electrode layer positioned on the face of the soft flexible foam rim for facing abutting contact with the patient's soft tissue, and an electrical connector positioned in the concave cap, electrically connecting the electrode layer to the current source, whereby the patient's soft tissue contacted by the electrode layer receives electrical current stimulation.

* * * * *